United States Patent
Pan

(10) Patent No.: US 10,699,664 B2
(45) Date of Patent: Jun. 30, 2020

(54) IMAGE DISPLAY SYSTEM AND METHOD OF TRANSFORMING DISPLAY PANELS OF MOBILE DEVICES INTO BEING COMPATIBLE WITH MEDICAL IMAGES DISPLAY STANDARD

(71) Applicant: EBM TECHNOLOGIES INCORPORATED, Taipei (TW)

(72) Inventor: William Pan, Taipei (TW)

(73) Assignee: EBM TECHNOLOGIES INCORPORATED, Taipei (TW)

( * ) Notice: Subject to any disclaimer, the term of this patent is extended or adjusted under 35 U.S.C. 154(b) by 247 days.

(21) Appl. No.: 15/961,837

(22) Filed: Apr. 24, 2018

(65) Prior Publication Data

US 2019/0122633 A1    Apr. 25, 2019

Related U.S. Application Data

(60) Provisional application No. 62/576,654, filed on Oct. 25, 2017.

(30) Foreign Application Priority Data

Feb. 9, 2018 (TW) .............................. 107104720 A

(51) Int. Cl.
G09G 5/00    (2006.01)
G09G 5/02    (2006.01)
G16H 30/20   (2018.01)

(52) U.S. Cl.
CPC .............. G09G 5/005 (2013.01); G09G 5/028 (2013.01); G16H 30/20 (2018.01);
(Continued)

(58) Field of Classification Search
CPC ...... G09G 3/3607; G09G 5/005; G09G 5/028; G09G 2320/0271; G09G 2320/0276;
(Continued)

(56) References Cited

U.S. PATENT DOCUMENTS

2002/0091659 A1* 7/2002 Beaulieu et al. ..... G06F 19/321
706/62
2014/0347251 A1 11/2014 Cho et al. ...................... 345/2.3

FOREIGN PATENT DOCUMENTS

CN    106485079 A    3/2017
JP    2003-319908 A    11/2003
(Continued)

OTHER PUBLICATIONS

Anonymous, DICOM—Wikipedia, pp. 1-11, XP055518369, Sep. 28, 2017.

*Primary Examiner* — Andrew W Johns
(74) *Attorney, Agent, or Firm* — Winston Hsu

(57) ABSTRACT

An image display system transforming LCD panels of mobile devices into being compatible with medical images display standard includes a host display panel, a slave mobile display device and a host computer. The host computer is coupled to the host display panel and the slave mobile display device for executing a process of sharing medical image, wherein the process of sharing medical image includes executing an image capture program to capture a color medical image, performing an image processing process to convert the color medical image into a grayscale medical image, converting the grayscale medical image into an image package, and connecting to the slave mobile display device to transmit the image package to the slave mobile display device.

15 Claims, 3 Drawing Sheets

(52) U.S. Cl.
CPC ..... *G09G 2320/04* (2013.01); *G09G 2340/06* (2013.01); *G09G 2360/04* (2013.01); *G09G 2380/08* (2013.01)

(58) Field of Classification Search
CPC ........... G09G 2320/04; G09G 2340/06; G09G 2340/145; G09G 2360/04; G09G 2380/08; G16H 30/20
See application file for complete search history.

(56) References Cited

FOREIGN PATENT DOCUMENTS

| | | | |
|---|---|---|---|
| JP | 2003-324737 | A | 11/2003 |
| JP | 2005-245828 | A | 9/2005 |
| JP | 2013-111092 | A | 6/2013 |
| JP | 2014-184068 | A | 10/2014 |
| JP | 2015-70999 | A | 4/2015 |
| KR | 10-1582795 | B1 | 1/2016 |
| TW | 200528068 | A | 9/2005 |
| TW | 200617847 | A | 6/2006 |
| TW | 200641725 | A | 12/2006 |
| TW | 201503678 | A | 1/2015 |

\* cited by examiner

IMAGE DISPLAY SYSTEM AND METHOD OF TRANSFORMING DISPLAY PANELS OF MOBILE DEVICES INTO BEING COMPATIBLE WITH MEDICAL IMAGES DISPLAY STANDARD

CROSS REFERENCE TO RELATED APPLICATIONS

This application claims the benefit of U.S. Provisional Application No. 62/576,654, filed on Oct. 25, 2017, the contents of which are incorporated herein.

BACKGROUND OF THE INVENTION

1. Field of the Invention

The present invention relates to an image display system and method, and more particularly, to an image display system and method capable of transforming LCD panels of mobile devices into being compatible with medical images display standard.

2. Description of the Prior Art

DICOM (Digital Imaging and Communications in Medicine) has defined file format and network communication protocols for medical images to handle image processing to digital medical images such as storage, print, and transmission, and so on. DICOM takes TCP (Transmission Control Protocol) and IP (Internet Protocol) as basic communication protocols to communication multiple network systems. For example, any medical equipment, server, workstation, display device, printer, and network equipment that supports DICOM format may transmit and receive digital medical images and patient data, and with DICOM format integrate abovementioned equipment and subsystems into a PACS (Picture archiving and communication system).

DICOM has also defined GSDF (Grayscale standard display function) standards for grayscale medical display devices. However, the grayscale medical display devices in the current market place are expensive and are fixed display devices (non-portable), which causes low popularity and is inconvenient to medical physicians to interpret medical image instantaneously. For example, the medical physicians must go to the fixed workstation and the grayscale medical display device to interpret the medical image.

As the mobile device (e.g., smart phone and tablet computer) become more and more popular and the advance of non-medical display devices, there are some non-medical display devices in the market place have the hardware specification and capability of displaying medical images. Therefore, the popularity of the medical image display device may be increased and the cost of building PACS may be decreased if non-medical display devices place have the hardware specification and capability of displaying medical images can be integrated into PACS.

However, how to share the medical images to the non-medical display devices having the hardware specification and capability of displaying medical images to integrate the non-medical display devices into PACS has become a new topic in the industry.

SUMMARY OF THE INVENTION

Therefore, the present invention relates to an image display system and method capable of transforming LCD panels of mobile devices into being compatible with medical images display standard.

The present invention discloses an image display system transforming LCD panels of mobile devices into being compatible with medical images display standard. The image display system includes a host display panel, a first slave mobile display device and a host computer. The host display panel is configured to display a first color medical image, wherein a host grayscale image conversion function of the host display panel complies with a grayscale standard display function defined by GSDF (Grayscale standard display function) standard. The host computer is coupled to a host display panel and the first slave mobile display device, and configured to execute a process of sharing medical image. The process of sharing medical image includes executing an image capture program to capture a first color medical image; performing an image processing process to convert the first color medical image into a first grayscale medical image; converting the first grayscale medical image into a first image package; and connecting to the first slave mobile display device to transmit the first image package to the first slave mobile display device, wherein a mobile device containing the first slave mobile display device has installed and executed a medical image display program.

The present invention further discloses a method of sharing medical image for an image display system transforming LCD panels of mobile devices into being compatible with medical images display standard, wherein the image display system comprises a host display panel, a first slave mobile display device and a host computer, wherein the method is compiled into a program and stored in a memory device of the host computer. The method includes capturing a first color medical image; converting the first color medical image into a first grayscale medical image according to an image processing process; converting the first grayscale medical image into a first image package; and transmitting the first image package to the first slave mobile display device, wherein a mobile device containing the first slave mobile display device has installed and executed a medical image display program.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
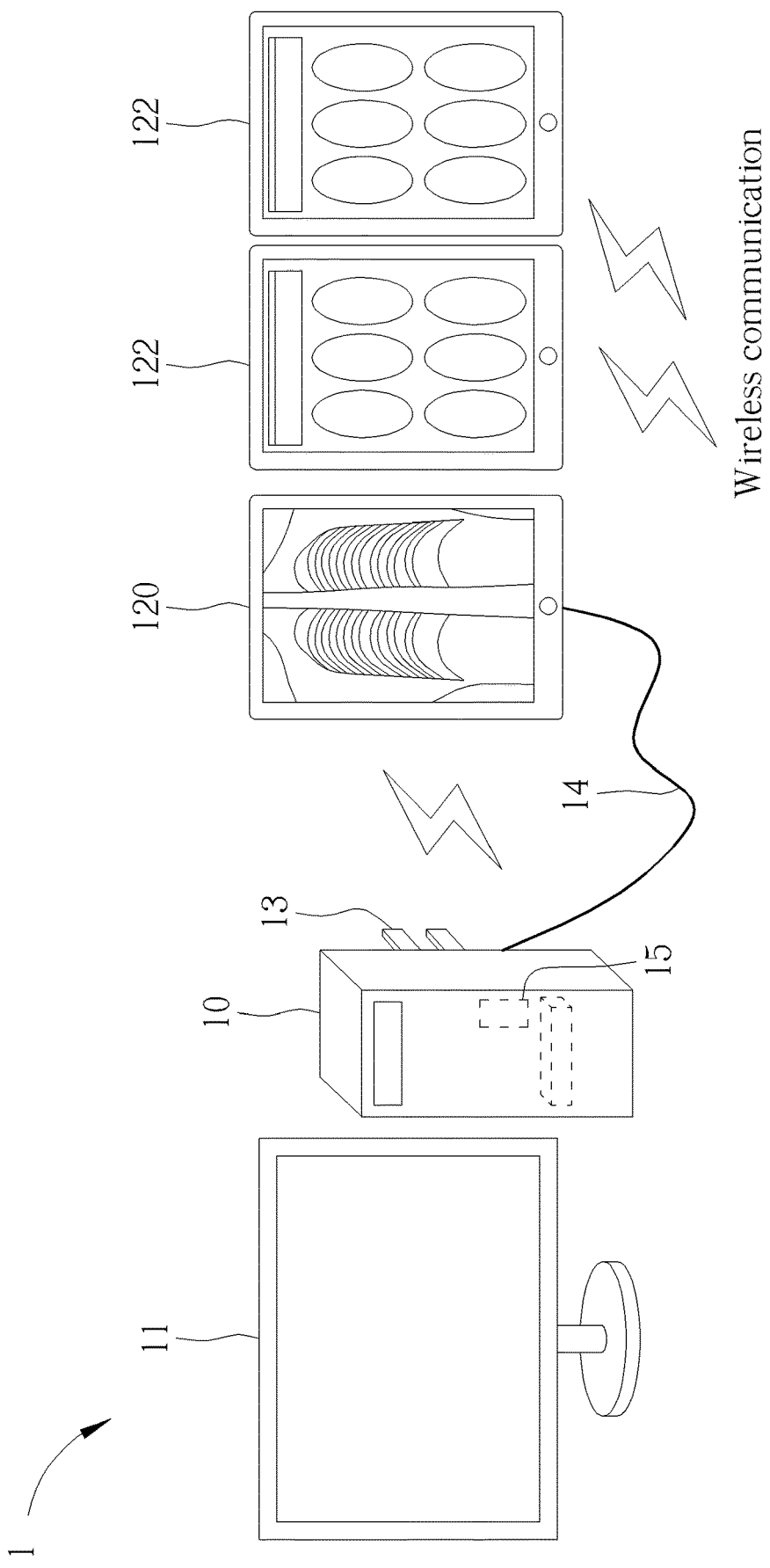
FIG. 1 is a schematic diagram of an image display system transforming LCD panels of mobile devices into being compatible with medical images display standard according to an embodiment of the present invention.

FIG. 1 is a schematic diagram of an image display system 1 transforming LCD (Liquid Crystal Display) panels of mobile devices into being compatible with medical images display standard according to an embodiment of the present invention. The image display system 1 includes a host computer 10, a host display panel 11, slave mobile display devices 120 and 122, and a dongle 13. The host computer 10 is coupled to the host display panel 11, the slave mobile display devices 120 and 122 and the dongle 13, and configured to execute an image capture program to capture medical images, and control the host display panel 11 to display the medical images. The image capture program is configured to read files (including medical images and patient data) comply with DICOM (Digital Imaging and Communications in Medicine) standard to retrieve the medical images. The host computer 10 may perform an image processing process to convert the digital medical images into an image package, and connect to the slave mobile display devices 120 and 122 to transmit the image package to the slave mobile display devices 120 and 122. The mobile devices including the slave mobile display devices 120 and 122 have to install and execute a medical image display program to connect to the host computer 10 and read the image package.

In detail, the host display panel 11 is coupled to the host computer 10, and configured to display the medical image and a user interface (e.g., desktop of an operating system, files, programs, and so on) of the host computer 10, and the host display panel 11 may be a standard medical diagnosis screen. The slave mobile display devices 120 and 122 may be display devices of mobile devices and non-standard medical diagnosis screens (e.g., screens of smart phones or tablet computers), wherein the slave mobile display devices 120 and 122 have to meet a hardware specification to be able to display the medical image. Differences between standard and non-standard medical diagnosis screens are shown in Table 1.

TABLE 1

| Specification | Medical diagnosis screen | Mobile device screen |
| --- | --- | --- |
| Panel Size | Usually 21 inches | Some are up to 13 inches |
| Resolution | At least 200 Megapixel | Some are greater than 500 Megapixel |
| Contrast | Must greater than 250 | Some are greater than 300 |
| DICOM GSDF | Mandatory | Non-mandatory |
| Portability | no | yes |
| Price | higher | lower |

Since the non-standard medical diagnosis screen is not designed based on GSDF (Grayscale standard display function) defined by DICOM to be lack of a grayscale image conversion function comply with DICOM. In other words, the grayscale image conversion function configured in the slave mobile display devices 120 and 122 does not comply with the grayscale standard display function defined by DICOM. In such a situation, before sharing the medical image to the slave mobile display devices 120 and 122, the grayscale image conversion function of the slave mobile display devices 120 and 122 must be reconfigured to comply with the grayscale standard display function defined by DICOM. As a result, the slave mobile display devices 120 and 122 are able to display the medical images with enough JND (Just-Noticeable Difference) for medical diagnosis.

Specifically, the host computer 10 may convert a color medical image into a host grayscale medical image according to the grayscale standard display function defined by DICOM or a host grayscale image conversion function of the host display panel 11, and configure the slave grayscale image conversion function of the slave mobile display devices 120 and 122 according to the host grayscale image conversion function, wherein the slave grayscale image conversion function is comply with grayscale standard display function defined by DICOM. Finally, the host computer 10 may generate a slave grayscale medical image and an image package according to the slave grayscale image conversion function and the host grayscale medical image. Therefore, when the image package of the slave grayscale medical image is received, the slave mobile display devices 120 and 122 may convert the slave grayscale medical image into the host grayscale medical image according to the slave grayscale image conversion function to display the host grayscale medical image complied with medical image display standards.

The dongle 13 is coupled to the host computer 10, and configured to operate as a virtual display device of the slave mobile display devices 120 and 122, which allows the slave mobile display devices 120 and 122 to be added to a device manager of the host computer 10, wherein the dongle 13 may process the image packages needed to be transmitted to the slave mobile display devices 120 and 122 by interfaces such as VGA (Video Graphics Array), DVI (Digital Visual Interface), HDMI (High Definition Multimedia Interface) and DP (Display Port), wherein the mobile devices containing the slave mobile display devices 120 and 122 have installed and executed the medical image display program to connect to the dongle 13 and read the image package.

In one embodiment, the image display system. 1 further includes a transmission line 14 configured to connect the host computer 10 and the slave mobile display device 120. The dongle 13 may transmit the image package to the slave mobile display device 120 by the transmission line, wherein the mobile device containing the slave mobile display device has installed and executed the medical image display program. In one embodiment, host computer 10 includes a wireless communication module 15, configured to connect to the slave mobile display device 122 by a wireless communication technology, e.g., Bluetooth, WiFi or NFC (Near Field Communication), wherein the mobile device containing the slave mobile display device has installed and executed the medical image display program.

In one embodiment, the host computer 10 may respectively share the first medical image and the second medical image to the slave mobile display devices 120 and 122, so the host display panel 11 may display a desktop or the first medical image (e.g., an extend mode that the slave mobile display devices 120 and 122 operate as extended display devices of the host display panel 11 and the host computer 10). Specifically, the host computer 10 may execute an image capture program to respectively capture the first medical image and the second medical image; perform the abovementioned image processing process to respectively convert the first medical image and the second medical image into the first grayscale medical image and the second grayscale medical image; respectively convert the first grayscale medical image and the second grayscale medical image into the first image package and the second image package; and respectively transmit the first image package and the second image package to the slave mobile display devices 120 and 122, wherein the mobile devices containing the slave mobile display devices 120 and 122 have installed and executed the medical image display program to read the first image package and the second image package.

In one embodiment, the host computer 10 may share the first medical image to the slave mobile display devices 120 and 122 (e.g., a mirror mode that the slave mobile display devices 120 and 122 operate as mirror display devices of the host computer 10 and the host display panel 11). Specifically, the host computer 10 may transmit the first image package corresponding to the first medical image to the slave mobile display devices 120 and 122, and the host display panel 11 also displays the same first medical image.

Therefore, the image display system 1 transforming LCD panels of mobile devices into being compatible with medical images display standard may integrate non-medical display device equipped with enough hardware specification into PACS (Picture archiving and communication system) to increase a popularity of the medical image display and reduce setup cost of PACS. In addition, by various methods of sharing images, the image display system 1 transforming LCD panels of mobile devices into being compatible with medical images display standard may realize extend mode and mirror mode, which is benefit for joint diagnosis for multiple medical physicians.

Figure 2:
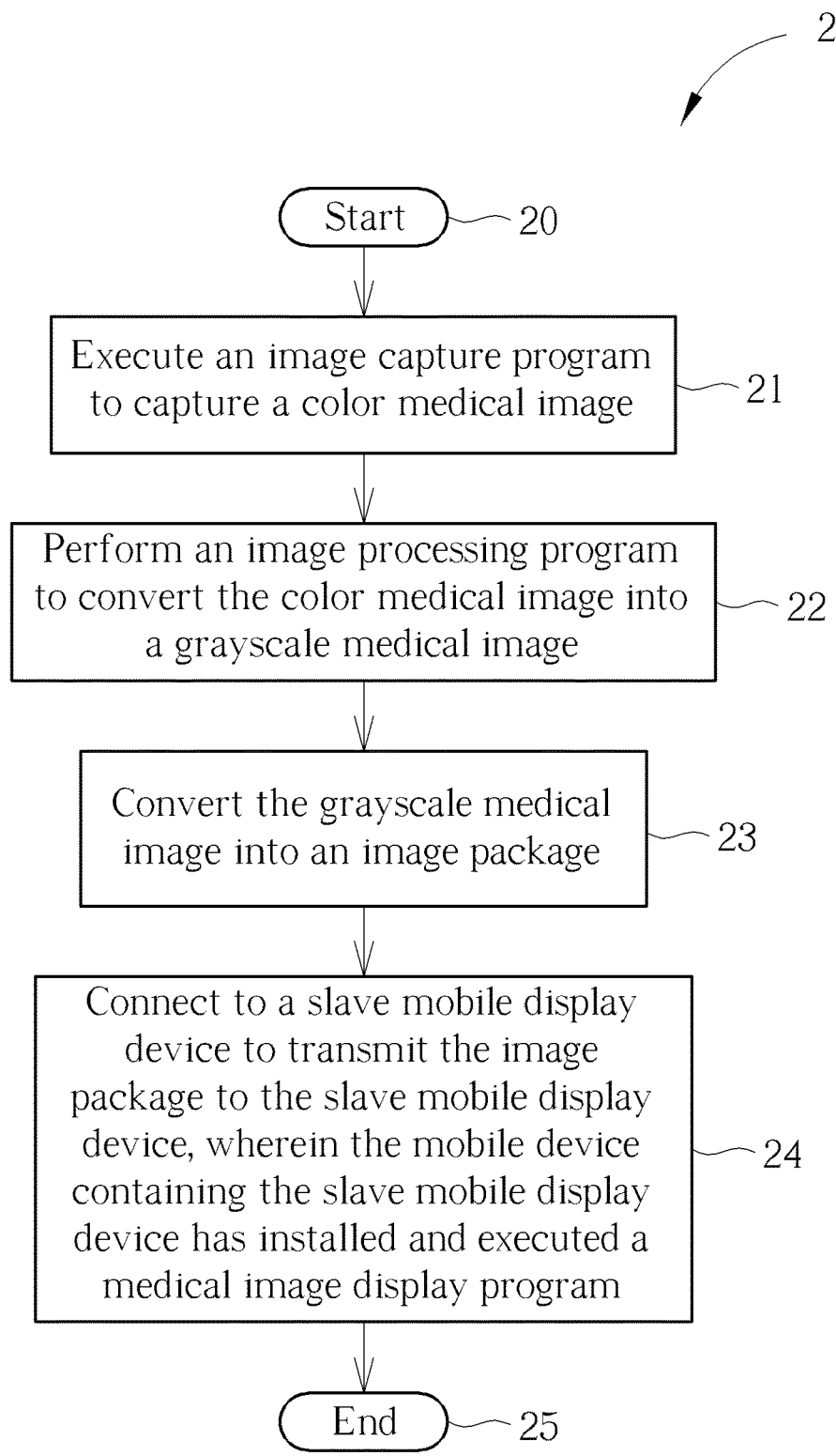
FIG. 2 is a flowchart of a process of sharing medical image according to an embodiment of the present invention.

Operations of the image display system 1 transforming LCD panels of mobile devices into being compatible with medical images display standard may be summarized into a process of sharing medical image 2. As shown in FIG. 2, the process of sharing medical image 2 may be compiled into a program code and stored in a built-in memory of the host computer 10 for instructing the host computer 10 to execute the following steps.

Step 20: Start.

Step 21: Execute an image capture program to capture a color medical image.

Step 22: Perform an image processing program to convert the color medical image into a grayscale medical image.

Step 23: Convert the grayscale medical image into an image package.

Step 24: Connect to a slave mobile display device to transmit the image package to the slave mobile display device, wherein the mobile device containing the slave mobile display device has installed and executed a medical image display program.

Step 25: End.

In the process of sharing medical image 2, a user may watch the desktop of the host display panel 11 (e.g., GUI (Graphical User Interface)) and input control signals to the host computer 10 by a user input interface (e.g., keyboard or mouse) to control the host computer 10 to perform Step 21 to Step 24. For example, the user may click a first icon for controlling generate a first control signal to control the host computer 10 to execute the image capture program to capture the first color medical image (Step 21), wherein the first icon corresponds to the image capture program. The user may click a second icon to generate a second control signal for controlling host the computer 10 to perform the image processing program (Step 22), wherein the second icon corresponds to the image processing program. The user may click a third icon to generate a third control signal for controlling the host computer 10 to convert the grayscale medical image into the image package (Step 23). Finally, the user may click a fourth icon to generate a fourth control signal for controlling the host computer 10 to connect to the slave mobile display device 120 or 122 to transmit the image package to the slave mobile display device 120 or 122, wherein the mobile device containing the slave mobile display device has installed and executed the medical image display program (Step 24), and the fourth icon corresponds to an image transmit program. For example, the slave mobile display device 120 or 122 may be integrated with the mobile device, and the mobile device may receive the image package by a built-in communication interface (e.g., wire or wireless communication interface). In addition, the mobile device may read image package when the medical image display program for the process of sharing medical image 2 is installed and in execution.

In one embodiment, the host computer 10 may connect to the slave mobile display devices 120 and 122 by the dongle 13 (Step 24). In one embodiment, the host computer 10 may further compresses the image package to generate a compressed image package, and then transmit the compressed image package to the slave mobile display device 120 or 122, which may reduce a file size of the image package to save memory space and speed up file sharing.

Therefore, by the process of sharing medical image 2, the image display system 1 transforming LCD panels of mobile devices into being compatible with medical images display standard may integrate non-medical display device (e.g., the slave mobile display devices 120 and 122) equipped with enough hardware specification into PACS (Picture archiving and communication system) to increase a popularity of the medical image display and reduce setup cost of PACS.

Figure 3:
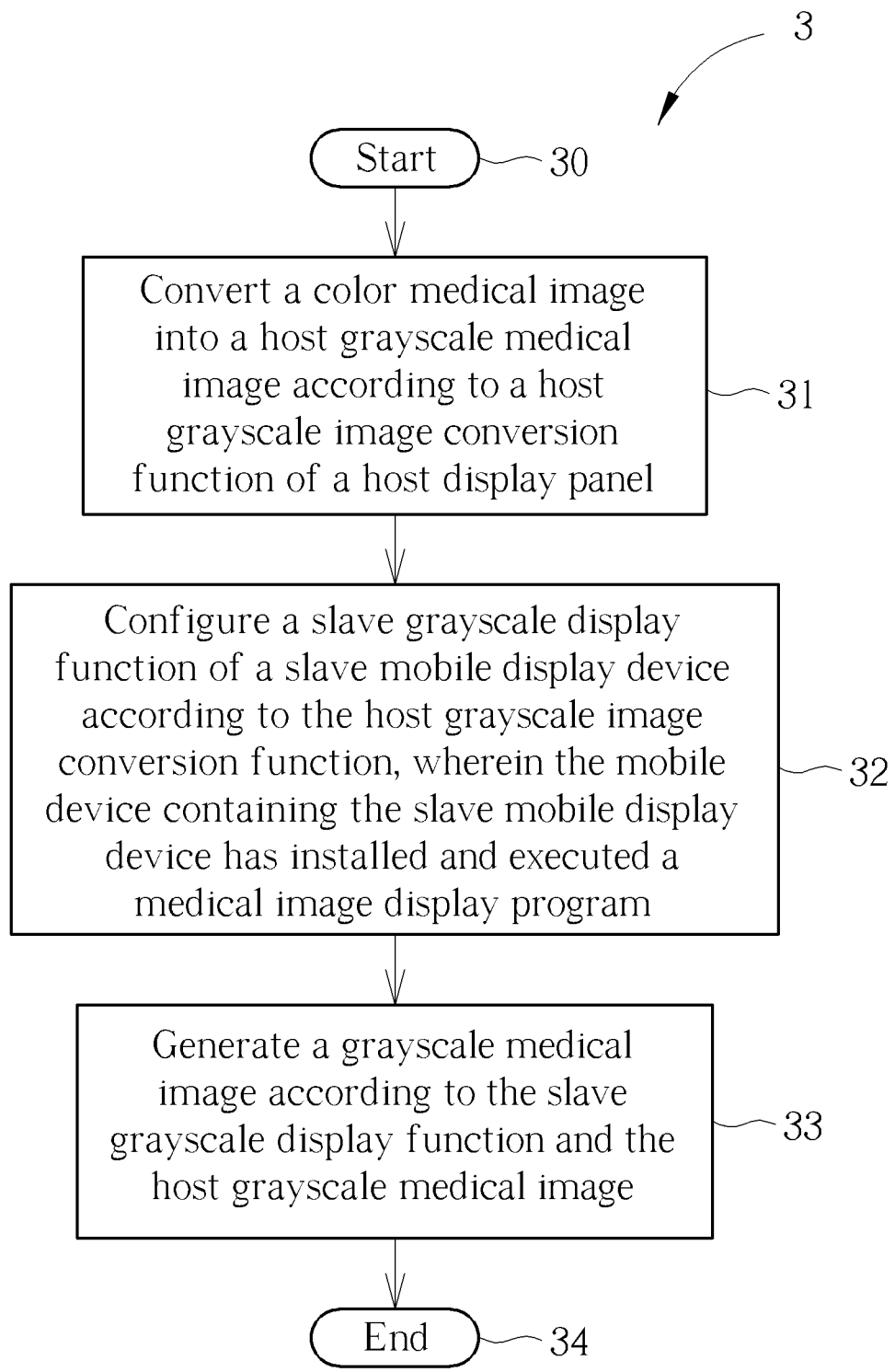
FIG. 3 is a flowchart of an image processing process according to an embodiment of the present invention.

In the process of sharing medical image 2, the image processing program of Step 22 may be summarized into an image processing process 3, as shown in FIG. 3, for instructing the host computer 10 to execute the following steps.

Step 30: Start.

Step 31: Convert a color medical image into a host grayscale medical image according to a host grayscale image conversion function of a host display panel.

Step 32: Configure a slave grayscale display function of a slave mobile display device according to the host grayscale image conversion function, wherein the mobile device containing the slave mobile display device has installed and executed a medical image display program.

Step 33: Generate a grayscale medical image according to the slave grayscale display function and the host grayscale medical image.

Step 34: End.

In the image processing process 3, the host computer 10 may convert the color medical image into the host grayscale medical image according to the host grayscale image conversion function (i.e., a grayscale image conversion function complied with medical image display standards) of the host display panel 11 (Step 31); then, configure the slave grayscale display function of the slave mobile display device 120 or 122 according to the host grayscale image conversion function of the host display panel 11, wherein the mobile device containing the slave mobile display device 120 or 122 have installed and executed the medical image display program (Step 32); finally, generate the slave grayscale medical image according to the slave grayscale display function and the host grayscale medical image (Step 33). Since the slave grayscale medical image includes the slave grayscale image conversion function, when the slave mobile display devices 120 and 122 receive the image package corresponding to the slave grayscale medical image, the slave mobile display devices 120 and 122 may convert the slave grayscale medical image into the host grayscale medical image according to the slave grayscale image conversion function, so as to display the grayscale medical image complied with medical image display standards.

Therefore, by the image processing process 3, the image display system 1 transforming LCD panels of mobile devices into being compatible with medical images display standard may generate the slave grayscale image conversion function to ensure that the slave mobile display devices 120 and 122 may display the grayscale medical image complied with medical image display standards.

To sum up, in the present invention, the image display system transforming LCD panels of mobile devices into being compatible with medical images display standard may integrate non-medical display device equipped with enough hardware specification into PACS (Picture archiving and communication system) to increase a popularity of the medical image display and reduce setup cost of PACS. In addition, by various methods of sharing images, the image display system 1 transforming LCD panels of mobile devices into being compatible with medical images display standard may realize extend mode and mirror mode, which is benefit for distant and joint diagnosis for multiple medical physicians.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An image display system transforming LCD panels of mobile devices into being compatible with medical images display standard, comprising:
   a host display panel configured to display a first color medical image, wherein a host grayscale image conversion function of the host display panel complies with a grayscale standard display function defined by GSDF (Grayscale standard display function) standard;
   a first slave mobile display device; and
   a host computer coupled to a host display panel and the first slave mobile display device, and configured to execute a process of sharing medical image, wherein the process of sharing medical image comprises:
      executing an image capture program to capture a first color medical image;
      performing an image processing process to convert the first color medical image into a first grayscale medical image;
      converting the first grayscale medical image into a first image package; and
      connecting to the first slave mobile display device to transmit the first image package to the first slave mobile display device, wherein a mobile device containing the first slave mobile display device has installed and executed a medical image display program.

2. The image display system transforming LCD panels of mobile devices into being compatible with medical images display standard of claim 1, wherein the image processing process comprises:
   converting the first color medical image into a host grayscale medical image according to a host grayscale image conversion function;
   configuring a slave grayscale image conversion function of the first slave mobile display device according to the host grayscale image conversion function; and
   generating the first grayscale medical image according to the slave grayscale image conversion function and the host grayscale medical image.

3. The image display system transforming LCD panels of mobile devices into being compatible with medical images display standard of claim 2, wherein the slave grayscale display function complies with a grayscale standard display function defined by the GSDF standard.

4. The image display system transforming LCD panels of mobile devices into being compatible with medical images display standard of claim 1, further comprising a second slave mobile display device, the process of sharing medical image comprises:
   executing an image capture program to capture a second color medical image;
   performing the image processing process to convert the second color medical image into a second grayscale medical image;
   converting the second grayscale medical image into a second image package; and
   transmitting the second image package to the second slave mobile display device, wherein a mobile device containing the second slave mobile display device has installed and executed the medical image display program.

5. The image display system transforming LCD panels of mobile devices into being compatible with medical images display standard of claim 1, further comprising a second slave mobile display device, the process of sharing medical image comprises:
   transmitting the first image package to the first slave mobile display device and the second slave mobile display device, wherein the mobile device containing the first slave mobile display device and the second slave mobile display device have installed and executed the medical image display program.

6. The image display system transforming LCD panels of mobile devices into being compatible with medical images display standard of claim 1, further comprising:
   a dongle coupled to the host computer, and configured to operate as a virtual display device of the first slave mobile display device, wherein the host computer connects to the first slave mobile display device by the dongle, and the dongle transmit the first image package to the first slave mobile display device according to one of interfaces comprising VGA (Video Graphics Array), DVI (Digital Visual Interface), HDMI (High Definition Multimedia Interface, HDMI) and DP (Display Port), and the mobile device containing the first slave mobile display device has installed and executed the medical image display program.

7. The image display system transforming LCD panels of mobile devices into being compatible with medical images display standard of claim 6, further comprising a transmission line configured to connect the host computer and the first slave mobile display device, the dongle transmits the first image package to the first slave mobile display device by the transmission line, and the mobile device containing the first slave mobile display device has installed and executed the medical image display program.

8. The image display system transforming LCD panels of mobile devices into being compatible with medical images display standard of claim 6, wherein the host computer comprises a wireless communication module, and the dongle transmits the first image package to the first slave mobile display device by the wireless communication module, and the mobile device containing the first slave mobile display device has installed and executed the medical image display program.

9. The image display system transforming LCD panels of mobile devices into being compatible with medical images display standard of claim 1, wherein the connecting to the first slave mobile display device to transmit the first image package to the first slave mobile display device comprises:
   compressing the first image package to generate a first compressed image package; and
   transmitting the first compressed image package to the first slave mobile display device, wherein the mobile device containing the first slave mobile display device has installed and executed the medical image display program.

10. A method of sharing medical image for an image display system transforming LCD panels of mobile devices into being compatible with medical images display standard, wherein the image display system comprises a host display panel, a first slave mobile display device and a host computer, wherein the method is compiled into a program and stored in a memory device of the host computer, and the method comprises:
- capturing a first color medical image;
- converting the first color medical image into a first grayscale medical image according to an image processing process;
- converting the first grayscale medical image into a first image package; and
- transmitting the first image package to the first slave mobile display device, wherein a mobile device containing the first slave mobile display device has installed and executed a medical image display program.

11. The method of sharing medical image of claim 10, wherein the image processing process comprises:
- converting the first color medical image into a host grayscale medical image according to a host grayscale image conversion function;
- configuring a slave grayscale image conversion function of the first slave mobile display device according to the host grayscale image conversion function; and
- generating the first grayscale medical image according to the slave grayscale image conversion function and the host grayscale medical image.

12. The method of sharing medical image of claim 11, wherein the slave grayscale display function complies with a grayscale standard display function defined by the GSDF standard.

13. The method of sharing medical image of claim 10, wherein the image display system transforming LCD panels of mobile devices into being compatible with medical images display standard further comprising a second slave mobile display device, the medical image share method comprises:
- capturing a second color medical image;
- converting the second color medical image into a second grayscale medical image according to the image processing process;
- converting the second grayscale medical image into a second image package; and
- transmitting the second image package to the second slave mobile display device, wherein a mobile device containing the second slave mobile display device has installed and executed the medical image display program.

14. The method of sharing medical image of claim 10, wherein the image display system transforming LCD panels of mobile devices into being compatible with medical images display standard further comprising a second slave mobile display device, the medical image share method comprises:
- transmitting the first image package to the second slave mobile display device, wherein a mobile device containing the second slave mobile display device has installed and executed the medical image display program.

15. The method of sharing medical image of claim 10, wherein transmitting the first image package to the first slave mobile display device comprises:
- compressing the first image package to generate a first compressed image package; and
- transmitting the first compressed image package to the first slave mobile display device, wherein the mobile device containing the first slave mobile display device has installed and executed the medical image display program.

* * * * *